United States Patent [19]

Roper

[11] Patent Number: 4,562,293
[45] Date of Patent: * Dec. 31, 1985

[54] SPIROKETONE PROCESS

[75] Inventor: Jerry M. Roper, Baton Rouge, La.

[73] Assignee: Ethyl Corporation, Richmond, Va.

[*] Notice: The portion of the term of this patent subsequent to Oct. 30, 2001 has been disclaimed.

[21] Appl. No.: 660,860

[22] Filed: Oct. 15, 1984

[51] Int. Cl.$^4$ ............................................. C07C 45/45
[52] U.S. Cl. .................................... 568/347; 568/315
[58] Field of Search ............... 564/395, 401, 389; 568/362, 347, 349, 315

[56] References Cited

U.S. PATENT DOCUMENTS 2,962,531 11/1960 Coffield .............................. 564/389
3,173,952 3/1965 Farrer ................................. 564/389
3,225,099 12/1965 Coffield .............................. 564/389
4,052,457 10/1977 Nagakura et al. ................. 568/349
4,480,133 10/1984 Roper ................................. 568/362

OTHER PUBLICATIONS

Hatchard, J.A.C.S., vol. 80, pp. 3640-3642 (1958).
McClure, J. Org. Chem., vol. 27, pp. 2365-2368 (1962).

Primary Examiner—James H. Reamer
Attorney, Agent, or Firm—Donald L. Johnson; John F. Sieberth; Patricia J. Hogan

[57] ABSTRACT

Spiro[5.5]undeca-1,4,8-trien-3-ones are prepared by reacting a phenol having a free p-position with formaldehyde, a nitrogen compound selected from ammonia and primary and secondary amines, and a conjugated diene in an inert solvent at a temperature of at least about 190° C.

13 Claims, No Drawings

SPIROKETONE PROCESS

FIELD OF INVENTION

This invention relates to spiroketones and more particularly to a process for preparing them.

BACKGROUND

Spiro[5.5]undeca-1,4,8-trien-3-ones are known compounds that are described in Hatchard, *Journal of the American Chemical Society*, Vol. 80, pp. 3640–3642 (1958); McClure, *Journal of Organic Chemistry*, Vol. 27, pp. 2365–2368 (1962); and copending applications Ser. No. 472,196 (Roper I) and Ser. No. 660,859 (Roper II), filed Mar. 4, 1983, and Oct. 15, 1984, in the name of Jerry M. Roper. As taught in Roper I, such spiroketones are of interest as antioxidants and/or as flame retardant, insecticide, or pharmaceutical intermediates; and they can be prepared by reacting a 4-aminomethylphenol with a conjugated diene and an alkyl halide, typically at a temperature in the range of about 50°–200° C., in an inert solvent. Roper II teaches that the reaction can be accomplished without the aid of an alkyl halide.

SUMMARY OF INVENTION

An object of this invention is to provide a novel process for preparing spiro[5.5]undeca-1,4,8-trien-3-ones.

Another object is to provide such a process which employs easily available chemicals as starting materials.

These and other objects are attained by reacting a phenol having a free p-position with formaldehyde, a nitrogen compound selected from ammonia and primary and secondary amines, and a conjugated diene in an inert solvent at a temperature of at least about 190° C. so as to form a spiro[5.5]undeca-1,4,8-trien-3-one.

DETAILED DESCRIPTION

Phenols utilizable in the practice of the invention are 2,6-disubstituted phenols having a free p-position. They are generally compounds corresponding to the formula:

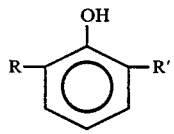

wherein R and R' are independently selected from hydrocarbyl groups containing 1–40 carbons. Such compounds include, e.g., 2-methyl-6-isopropyl-, 2-methyl-6-t-butyl-, 2-ethyl-6-t-butyl-, 2,6-dimethyl-, 2,6-diethyl-, 2,6-diisopropyl-, 2,6-di-sec-butyl-, 2,6-di-t-butyl-, 2,6-diheptyl-, and 2,6-dioctylphenols; etc. The compounds that are preferred vary with the particular end products desired but are generally the compounds of the above formula wherein R and R' are independently selected from alkyl groups containing 1–6 carbons.

The formaldehyde may be reacted with the phenol in any suitable form but is generally employed in the form of paraformaldehyde. Its concentration in the reaction mixture should be at least about equimolar, and it is generally preferred to employ about 1–10 mols of formaldehyde per mol of the phenol.

The nitrogen compound used in the practice of the invention is generally a compound corresponding to the formula:

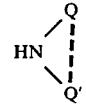

wherein Q and Q', when separate, are independently selected from hydrogen and hydrocarbyl groups containing 1–20 carbons and, when joined together, form a ring with the nitrogen to which they are attached, usually a five- or six-membered ring. Exemplary of such compounds are ammonia; piperidine; morpholine; pyrrolidine; methyl-, ethyl-, octyl-, dimethyl-, diethyl-, dioctyl-, ethylmethyl-, octylmethyl-, etc., amines, and the like. The preferred amines are dialkylamines wherein the alkyl groups contain 1–6 carbons. This ingredient of the reaction mixture is usually employed in an amount such as to provide a nitrogen compound/phenol mol ratio in the range of about 0.05–10/1.

Conjugated dienes that can be reacted with the phenols are generally compounds corresponding to the formula:

$$CHR_1=CR_2-CR_3=CHR_4$$

wherein $R_1$, $R_2$, $R_3$, and $R_4$ are independently selected from hydrogen and alkyl, cycloalkyl, and aralkyl groups containing 1–8 carbons. The diene that is preferred varies with the particular end product desired but is generally 1,3-butadiene. Other suitable dienes include, e.g., 2-methyl-1,3-butadiene, 2,3-di-methyl-1,3-butadiene, 2,3-diethyl-1,3-butadiene, 2,3-dipentyl-1,3-butadiene, 1,3-pentadiene, 1,3-hexadiene, 1,3-octadiene, 2,4-hexadiene, 2,4-heptadiene, 3,5-octadiene, 2-methyl-1,3-pentadiene, 2,3-dimethyl-1,3-pentadiene, 3-methyl-2,4-hexadiene, 3,4-dimethyl-2,4-hexadiene, 4-methyl-3,5-octadiene, 4,5-dimethyl-3,5-octadiene, 1-phenyl-1,3-butadiene, 2-phenyl-1,3-butadiene, 1,4-diphenyl-1,3-butadiene, 1-phenyl-1,3-pentadiene, 1-phenyl-1,3-hexadiene, 1-phenyl-1,3-heptadiene, 1-phenyl-1,3-octadiene, 1,6-diphenyl-2,4-hexadiene, 1-cyclohexyl-1,3-butadiene, 2-cyclohexyl-1,3-butadiene, 2,3-dicyclohexyl-1,3-butadiene, etc. Ordinarily, the amount of conjugated diene employed is in the range of about 1–10 mols per mol of the phenol.

Solvents employed in the practice of the invention may be any solvents that are inert under the reaction conditions but are generally aprotic solvents. Such solvents include, e.g., hydrocarbons, especially aromatic hydrocarbons such as benzene, toluene, etc.; halogenated hydrocarbons such as tetrachloroethane, chlorinated benzenes and toluenes, etc.; lower alkanols such as methanol, ethanol, t-butyl alcohol, isohexyl alcohol, etc.; dipolar aprotic solvents such as dimethyl sulfoxide, N,N-dimethylformamide, etc. Among the preferred solvents is isopropyl alcohol.

The reaction is conducted by combining the components of the reaction mixture and heating them at a temperature of at least about 190° C. for a time sufficient to provide the desired product, usually about 4–30 hours. When reaction temperatures above the boiling point of the conjugated diene are utilized, the reaction is conducted under pressure, e.g., a pressure of about 10–1000 psig, to prevent volatilization; and temperatures higher than about 500° C. are generally avoided to prevent excessive decomposition of the reactants. It is generally preferred to conduct the reaction under substantially anhydrous conditions to optimize the reaction rate and yield.

The reaction proceeds via in situ formation of a Mannich base which subsequently thermally eliminates amine to afford a quinone methide intermediate that then undergoes a 4+2 cycloaddition in the presence of the conjugated diene to give a spiro[5.5]undeca-1,4,8-trien-3-one as the cycloadduct. As in the process of Roper, the spiro[5.5]undeca-1,4,8-trien-3-ones generally correspond to one of the formulas:

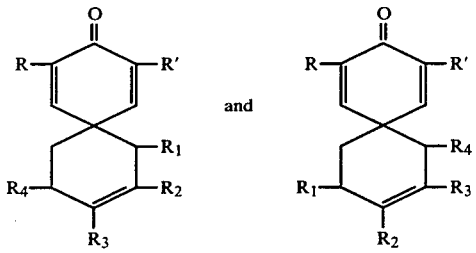

wherein R, R', $R_1$, $R_2$, $R_3$, and $R_4$ have the same meanings as those given above. It is an advantage of this invention that these products are prepared without the aid of an alkyl halide reactant and with the use of easily available chemicals as starting materials.

The following examples are given to illustrate the invention and are not intended as a limitation thereof.

EXAMPLE I

A mixture containing 60 mmols of paraformaldehyde, 50 mmols of 2,6-diisopropylphenol, and about 25 mmols of aqueous dimethylamine in 81 g of isopropyl alcohol was charged to a 300 mL Parr autoclave, which was sealed and evacuated by a water aspirator and then charged with 100 mmols of 1,3-butadiene. The reaction mixture was heated to 195° C. and held at 195°–205° C. for 6–7 hours, during which a maximum pressure of 400 psig was obtained. After cooling the reaction mixture was worked up to provide a reddish solid which was identified by NMR and GC as 2,4-diisopropylspiro[5.5]undeca-1,4,8-trien-3-one. Purification by vacuum distillation at 130°–139° C. (2.5 mm Hg) provided the product as a colorless oil which solidified to a colorless solid upon standing.

EXAMPLE II

Following the same general procedure as in Example I, 50 mmols of 2,6-dimethylphenol were reacted with 55 mmols of paraformaldehyde, 12.5 mmols of aqueous dimethylamine, and 100 mmols of 1,3-butadiene in 54 g of isopropyl alcohol at about 190° C. for 9–10 hours. The process resulted in the formation of 2,4-dimethylspiro[5.5]undeca-1,4,8-trien-3-one.

EXAMPLE III

Following the same general procedure as in Example I, 50 mmols of 2,6-diisopropylphenol were reacted with 75 mmols of paraformaldehyde, 75 mmols of aqueous dimethylamine, and 210 mmols of 1,3-butadiene in 100 g of isopropyl alcohol at 190°–200° C. for five hours. The process resulted in the formation of 2,4-diisopropylspiro[5.5]undeca-1,4,8-trien-3-one.

It is obvious that many variations can be made in the products and processes set forth above without departing from the spirit and scope of this invention.

I claim:

1. A process which comprises reacting a phenol having a free p-position with formaldehyde, a nitrogen compound selected from ammonia and primary and secondary amines, and a conjugated diene in an inert solvent at a temperature of at least about 190° C. so as to form a spiro[5.5]undeca-1,4,8-trien-3-one.

2. The process of claim 1 wherein the phenol is a compound corresponding to the formula:

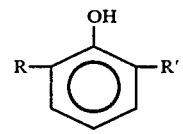

in which R and R' are independently selected from hydrocarbyl groups containing 1–40 carbons.

3. The process of claim 2 wherein R and R' of the phenol formula are independently selected from alkyl groups containing 1–6 carbons.

4. The process of claim 1 wherein the formaldehyde is employed in the form of paraformaldehyde.

5. The process of claim 1 wherein the nitrogen compound is a compound corresponding to the formula:

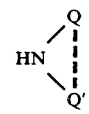

in which Q and Q', when separate, are independently selected from hydrogen and hydrocarbyl groups containing 1–20 carbons and, when joined together, form a ring with the nitrogen to which they are attached.

6. The process of claim 5 wherein Q and Q' of the formula are independently selected from alkyl groups containing 1–6 carbons.

7. The process of claim 1 wherein the conjugated diene is a compound corresponding to the formula $CHR_1=CR_2—CR_3=CHR_4$, in which $R_1$, $R_2$, $R_3$, and $R_4$ are independently selected from hydrogen and alkyl, cycloalkyl, and aralkyl groups containing 1–8 carbons.

8. The process of claim 7 wherein the conjugated diene is 1,3-butadiene.

9. The process of claim 1 wherein the inert solvent is an aprotic solvent.

10. The process of claim 9 wherein the solvent is isopropyl alcohol.

11. The process of claim 1 wherein the reaction is conducted at about 190°–500° C.

12. A process which comprises reacting (A) a phenol corresponding to the formula:

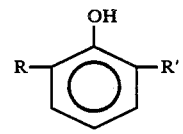

with (B) formaldehyde, (C) a nitrogen compound corresponding to the formula:

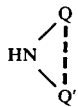

and (D) a conjugated diene corresponding to the formula:

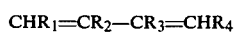

in an inert solvent at a temperature of about 190°–500° C. so as to form a spiro[5.5]undeca-1,4,8-trien-3-one; R and R' being independently selected from hydrocarbyl groups containing 1–40 carbons; Q and Q', when separate, being independently selected from hydrogen and hydrocarbyl groups containing 1–20 carbons and, when joined together, forming a ring with the nitrogen to which they are attached; and $R_1$, $R_2$, $R_3$, and $R_4$ being independently selected from hydrogen and alkyl, cycloalkyl, and aralkyl groups containing 1–8 carbons.

13. The process of claim 12 wherein R, R', Q, and Q' are independently selected from alkyl groups containing 1–6 carbons, and the conjugated diene is 1,3-butadiene.

* * * * *